(12) United States Patent
Lovoi

(10) Patent No.: US 7,578,780 B2
(45) Date of Patent: *Aug. 25, 2009

(54) BRACHYTHERAPY APPLICATOR FOR DELIVERY AND ASSESSMENT OF LOW-LEVEL IONIZING RADIATION THERAPY AND METHODS OF USE

(75) Inventor: Paul A. Lovoi, Saratoga, CA (US)

(73) Assignee: Xoft, Inc., Sunnyvale, CA (US)

( * ) Notice: Subject to any disclaimer, the term of this patent is extended or adjusted under 35 U.S.C. 154(b) by 182 days.

This patent is subject to a terminal disclaimer.

(21) Appl. No.: 11/324,772

(22) Filed: Dec. 31, 2005

(65) Prior Publication Data

US 2006/0173233 A1    Aug. 3, 2006

Related U.S. Application Data

(63) Continuation-in-part of application No. 10/464,140, filed on Jun. 18, 2003, now Pat. No. 7,322,929.

(51) Int. Cl.
*A61N 5/00* (2006.01)

(52) U.S. Cl. .......................................... 600/3

(58) Field of Classification Search .................. 600/1–8
See application file for complete search history.

(56) References Cited

U.S. PATENT DOCUMENTS

| | | | |
|---|---|---|---|
| 6,149,575 A * | 11/2000 | Leonhardt | 600/4 |
| 6,251,059 B1 * | 6/2001 | Apple et al. | 600/3 |
| 6,320,935 B1 * | 11/2001 | Shinar et al. | 378/119 |
| 6,402,689 B1 * | 6/2002 | Scarantino et al. | 600/300 |
| 6,746,465 B2 * | 6/2004 | Diederich et al. | 606/192 |
| 7,322,929 B2 | 1/2008 | Lovoi | |
| 2005/0038468 A1 | 2/2005 | Panetta et al. | |
| 2005/0080340 A1 | 4/2005 | Stewart et al. | |
| 2005/0101824 A1 | 5/2005 | Stubbs | |
| 2006/0173233 A1 | 8/2006 | Lovoi | |

OTHER PUBLICATIONS

Gladstone, DJ and Chin, LM, "Automated data collection and analysis system for MOSFET radiation detectors", Med. Phys., May 1991, vol. 18(3).

Scarantino, Ruslander et al., "An implantable radiation dosimeter for use in external beam radiation therapy", Med. Phys., Sep. 2004, vol. 31(9), Sicel Technologies, Inc., Morrisvile, N.C.

Scarantino, Rini et al., "Initial clinical results of an in vivo dosimeter during external beam radiation therapy", Med. Phys., Jun. 1, 2005, vol. 62(2), Sicel Technologies, Inc., Morrisville, N.C.

"Treating Cancer From The Inside Out", 2004, Varian Medical Systems.

* cited by examiner

*Primary Examiner*—John P Lacyk
(74) *Attorney, Agent, or Firm*—Thomas M. Freiburger

(57) ABSTRACT

Applicators for ionizing radiation therapy and their methods of use are provided for expedient preparation of precise treatment plans and for quantitative assessment of therapy delivered to natural or surgically-created, intra-corporeal cavities or lumina. Feedback capability is provided for timely treatment control and for verification of treatment to plan using sensors on the applicators.

12 Claims, 3 Drawing Sheets

BRACHYTHERAPY APPLICATOR FOR DELIVERY AND ASSESSMENT OF LOW-LEVEL IONIZING RADIATION THERAPY AND METHODS OF USE

This application is a continuation-in-part of application Ser. No. 10/464,140, filed Jun. 18, 2003, now U.S. Pat. No. 7,322,929.

BACKGROUND OF THE INVENTION

This invention concerns the treatment of breast cancer or otherwise sited cancer, and an applicator capable of feeding back dose data during treatment. The invention also encompasses an efficient procedure for preparation of a radiation treatment plan, and verification and real-time control of treatment to plan following surgical tumor excision.

In treating cancer of the breast, as well as cancer found in other areas of the human body, with the patient under anesthesia, the tumor is surgically excised (with some surrounding tissue) and then typically, the surgical wound is closed and the patient is sent home pending determination of pathology of the excised tumor margins. The need for further excision is evaluated, and if necessary, carried out. A radiation treatment plan is then developed and the patient, in a series of later visits, is subjected to radiation treatment in the volume of tissue surrounding the excised tumor. This can often involve re-opening of the surgical cavity for insertion of an applicator for use with ionizing radiation sources, i.e. radioactive isotopes. The forming of a radiation treatment plan under these circumstances is usually a several-hour process that can require imaging of the excision cavity, to determine its shape and location in the body, using external devices such as magnetic resonance imaging or CT scanning equipment. Transfer of data is then needed between the imaging equipment and the treatment planning software for preparing a plan of irradiation, with the need to verify transferred data values to check for errors.

These several steps involve considerable time and associated costs and make intraoperative radiation treatment logistically difficult if not impossible. In the case of breast tumors, moving of the patient for imaging is a problem in itself, because the breast tissue is mobile and the excision cavity may move. There is a need for methodology which would allow intraoperative radiation treatment of breast cancer and other cancers, without moving the patient, without requiring external imaging devices and without waking the patient from anesthesia.

There is also a need for increased precision in delivering radiation to a volume of tissue following surgery, to closely follow a physician's prescription. For example, more versatility and accuracy are needed in avoiding damage to skin in irradiation of breast tissue, and avoiding damage to the heart, lungs and bones, while still delivering prescribed dosage where needed. Over-radiation of any tissue areas is to be avoided as much as possible.

The determination of a treatment plan depends on obtaining information on the shape and location of the excision cavity and the need to avoid damage to other areas of tissue (such as the skin, the chest wall, lungs and heart). Intraoperative radiation treatment has generally not been possible or practical for several reasons: the need to move the patient to the location of imaging equipment, to obtain the imaging data and transfer that data to a form useable in applicator equipment for performing the irradiation; and the need to obtain data on pathology of the excised tissue or the remaining tissue in the excision cavity, prior to executing a treatment plan. Obtaining these needed data requires considerable time; in general a patient following tumor excision should be ready for radiation treatment within about ½ hour, certainly less than 1 hour, and this is not possible with current procedures and equipment.

Current applicators comprise balloons with defined shapes, usually spherical, which can be filled to the appropriate size for the particular cavity, but beyond this size and shape, variation adjustment typically is not possible. The surgeon needs to cut as near-spherical an excision as possible to enable the proper use of the device. With the applicator in the excision cavity and filled, the patient's breast is imaged by exterior imaging equipment. This imaging not only determines the size of the inflated applicator within the breast excision cavity, but also enables the physician to look at any gaps between the applicator and the tissue at the boundaries of the excision cavity. Seroma from the wound may lie between the applicator and the cavity walls. 90% to 95% contact between the applicator and the excision cavity is required to ensure proper radiation delivery. If the applicator/tissue contact is sufficient, the physician uses a table to look up the needed dwell time for the diameter of the applicator and for the particular, known activity of the radio isotope source. The ionizing radiation source, i.e. an iridium ($^{192}$Ir) wire on the end of a stainless steel guide wire, is inserted into the middle of the applicator for the prescribed duration. This works because the reference table for the source accounts for radiation intensity decay as a function of distance from the source location.

Proxima Therapeutics, Inc. has developed a procedure of this sort. The Proxima procedure is based on a known geometry, i.e. a spherical shape of the applicator and cavity. The equipment is not adaptable to an irregularly-shaped excision cavity. Moreover, the applicator and procedure are not useful for smaller-sized tumors, because of unacceptable surface-to-depth ratio of radiation dosage at near ranges of the radiation source.

In view of the above description of current methods, there is clearly a need for a system and applicator to facilitate expeditious creation of an ionizing radiation treatment plan, delivery of brachytherapy in accordance with that plan, and verification that such treatment was delivered, all in a manner to assure comfort and convenience to a patient. Further there is need for a system capable of post-excision treatment of small, early-stage cancers.

SUMMARY OF THE INVENTION

Although the apparatus and methods of this invention are pertinent to radiation therapy utilizing natural radio-isotope sources, the applicator of this invention is preferably for use with systems like those described in copending patent application Ser. No. 10/464,140 in which small electronic x-ray sources are utilized in post-operative treatment of proliferative cell disease, and in particular, after breast lumpectomy. Such electronic x-ray sources have the advantage of being controllable by varying input voltage and current, or for that matter, interrupting their radiation output entirely, all of which can be utilized for control of radiation emitted.

In excising a tumor, it is preferable that the surgeon be able to follow the tumor itself in order to minimize the tissue being excised, and not to have to create an arbitrary cavity shape in order to accommodate a particular balloon applicator. Cavities which result from tumor resection are often irregular in shape, with one axis often being longer than others. This sort of shape leads to a preference for treating such cavities from a series of known source positions and by multiple radiation exposures. Since individual radiation sources have known decay functions with distance as explained above, irregular shapes also reinforce the need for balloons which accommodate the cavity created, conforming to the marginal tissue. Balloons providing this characteristic behavior are generally elastic, and assuming appropriate geometry, will assume the shape of the cavity to be treated upon inflation.

The system, of which the applicator of this invention is a part, comprises a source of radiation, a processor to track location of the source through a sequence of known positions within the cavity which is surrounded by the tissue volume to be treated, and to monitor the dwell in each position. The processor is preferably accompanied by a controller to automatically advance the source and time its dwell sequentially, but conversely, actuation may be by hand in response to commands by the processor. Where the radiation source is a small x-ray tube, there is additionally a power supply to drive the x-ray tube in response to parameters developed in the treatment plan.

A preferred applicator comprises a tubular shaft having an inflatable balloon at its distal end, and serves the purpose of positioning one or a plurality of sources and one or a plurality of radiation sensors in sequences of known positions within the cavity relative to the tissue receiving treatment. Each sensor has wiring or wireless means to communicate with the external elements of the system in order to communicate dosimetry values to the therapist or to automated apparatus within the system. Preferably, the balloon is substantially transparent to ionizing radiation, and is a cavity-filling balloon. One preferred embodiment of an applicator is an array of source guides positioned on the surface of the inflatable balloon, each lying on adjacent planes, all of which preferably pass through a common and substantially central axis of the balloon, the adjacent planes being separated from each other by arbitrary angles. In addition, the applicator comprises a sensor guide on the substantially central axis. At the proximal end of the balloon, all guides follow or pass within the shaft to a region outside of the patient. Once outside the patient, all guides continue to the controller. Any conductors necessary to pass dosimetry information from the sensor(s) continues to the processor, and the power wiring for the radiation source(s) continues to the power supply, controlled by the processor. The shaft also comprises a lumen and proximal (outside the body) and distal (within the balloon) ports for inflating the balloon. Through the shaft, and guides, sources may be introduced into or onto the balloon and manipulated from outside of the patient after the balloon is inserted into the cavity and inflated.

The procedure for creating the treatment plan may comprise the following steps. A series of incremental locations for each guide within or on the balloon are selected. A greater number of locations will in general increase the precision of the plan created, and fewer locations conversely. A sensor is introduced into the balloon in the axis guide and an electronic source is introduced into a source guide and advanced onto the surface of the deflated balloon. A trial dose of radiation (at the operating voltage but at low current) is emitted from the source and detected quantitatively at the sensor. Since the sensor is immediately adjacent to the source in the deflated balloon configuration, this reading verifies the source output in relation to its power input. If a previous calibration of the source is available and satisfactory, this calibration step may be omitted. The balloon is then inflated to fill the cavity, positioning the sensor substantially centrally within the balloon and the source at the surface of the tissue to be treated. Using the decay or dose-depth characteristic for the source (inverse square relationship), the distance from source to sensor is determined, as is the probable error associated with that distance measurement. The source location is then incremented to the next position, and the procedure repeated. Multiple electronic sources could be used if desired, operated in a quick sequence to obtain the mapping data efficiently. This process continues until every permutation of source and sensor distance and error has been measured. Since each distance measured defines a spherical locus of points about the sensor at each of the sequence of sensor locations, the shape of the cavity and the intensity of radiation delivered to each tissue surface location from each source position can be determined. Copending application Ser. No. 10/464,140 describes how, as noted above, a multiplicity of sources and a sensor may be used to speed up the determination of cavity shape and radiation intensity by location described above. Since the multiplicity of readings creates redundancy, analysis of probable errors associated with each distance on the surface of the balloon can be used to determine the expected error in the calculated shape of the cavity and therefore in the dose intensity which will result from a treatment plan. By increasing the number of location permutations, the expected error can be made acceptably small.

The data collected as described above are used in preparation of a treatment plan, wherein the therapist prescribes the local dose, taking account of desired treatment levels for potentially diseased tissue, and radiation resistance of normal tissue which must be protected. The processor then computes the treatment plan to fit the prescription values, taking into account the cumulative radiation incident from each of the specified source locations as it will be received from each source location specified in the treatment. Since the intensity-versus-distance function is known and applicable to each positive end source, precise dosage planning for each position can be programmed.

During treatment, whether fractional or complete, additional sensor readings may be taken for verification of treatment to plan. Variances from plan may be signaled to the therapist or to automated portions of the system such that corrections may be made. Such corrections may be made between fractions administered, or if desired, they may be made in real time as a treatment session proceeds. In either event these corrections, if made before compilation of the treatment plan, are referred to as real-time adjustments or corrections.

The applicator described above comprises sources traversed through known positions on the surface of the balloon, monitored by a sensor substantially confined to an axis of the balloon. An applicator in which the source is on the axis and sensors traverse on the balloon surface is equally feasible, as described below. With this embodiment, additional fixed radiation sensors may optionally be located on the skin or interstitially adjacent the cavity and may be used as additional sensor locations in determination of and radiation of the treatment plan. In fact, any arrangement of sensors and sources is practical in which the locations are defined for purposes of distance determination and from which incident radiation dose on the tissue surface in response to radiation emitted from the source by location within the cavity can be deduced.

A central-source applicator of this invention comprises a tubular applicator shaft with an inflatable balloon mounted surroundingly adjacent the distal end of the shaft and extending proximally. Preferably, the balloon is generally coaxial with the shaft, bonded to the distal end of the shaft and to the shaft at a point proximal of the distal end. A lumen or channel within the shaft traverses between a port within the balloon and an inflation port at or near a hub at the proximal end of the shaft, which in use will lie outside of the patient. Again the balloon is preferably elastic so as to conform to the target cavity, is transparent to ionizing radiation, and has on its surface an array of guide tubes into which sensors may be positioned and translated along the length of the inflated balloon. The shaft also provides a central lumen or guide for positioning the source and translating it along the axis for the length of the inflated balloon. Silicone rubber is a suitable material for the balloon and for silicone rubber tubes bonded on the balloon surface as sensor guides, or the sensors can be fixed to the balloon surface. The method of use with this embodiment of the invention is substantially the same as that described previously, but in this case, the source is positioned in the central guide and the sensor(s) at the balloon surface, and with the sensors located directly at the tissue greater accuracy in real-time tissue dose treatment can be expected. Further elaboration of this embodiment is described below.

DESCRIPTION OF PREFERRED EMBODIMENTS

Figure 1:
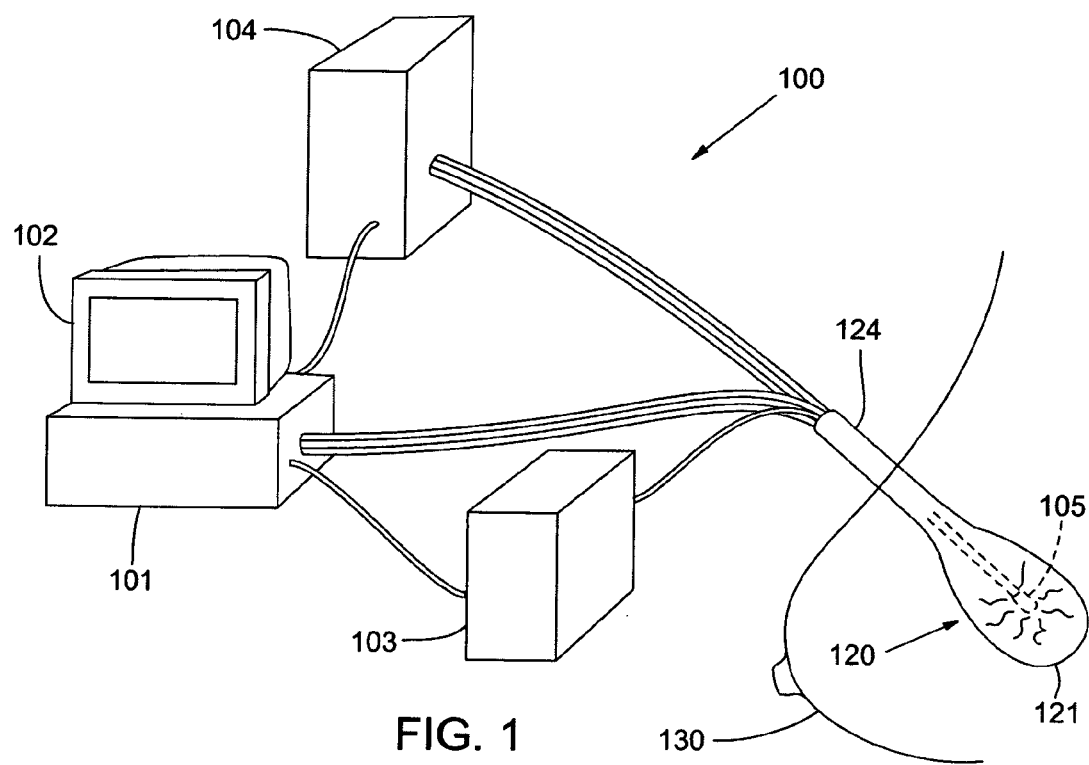
FIG. 1 shows schematically the system in which the applicator of the invention operates in relation to a breast and to other system elements.

The system 100 shown in FIG. 1 comprises a processor 101 for making computations based on inputs from other system elements and from the therapist, for indicating system conditions, coordinating and commanding actions of other system components, and for communicating information to the therapist, for example by monitor 102 or alternately, by printed means. Where the radiation source is a miniature x-ray tube (or tubes), a power supply 103 is provided to power the tube (or tubes) in response to commands from the processor. Preferably the system includes a controller 104 to mechanically manipulate the elements of an applicator 120 when the applicator is placed within a tissue volume of the patient for delivery of therapeutic ionizing radiation. The controller acts upon commands from the processor. In the schematic representation of FIG. 1, the applicator 120 is shown positioned in a post-operative cavity within a breast 130. If a controller is not included in the system, manipulation of the applicator 120 and its elements may be done by hand methods following commands communicated from the processor, for example as indicated on the screen of the monitor 102.

The power supply 103 provides high voltage and filament current for driving the x-ray tube 105, shown positioned generally centrally within the applicator balloon 121, in response to commands from the processor 101. If required to drive the x-ray tube 105, the power supply 103 may also provide laser energy, for example to heat the x-ray tube cathode. An example of such an x-ray source is described in U.S. Pat. No. 6,319,188. Generally, miniature x-ray sources consist of a flexible, high-voltage cable connected to a power source and controller at its proximal end and to the small x-ray tube at its distal end. The x-ray tube has a cathode which can be caused to emit electrons (for example by heat) at its proximal end and a target anode at its distal end. As typical, the voltage between the cathode and electrode accelerates the electrons emitted by the cathode such that they impact the anode creating x-rays. The spectrum of energies produced is related to the voltage applied between the anode and cathode and the target material used. It is this anode-to-cathode high voltage that provides the option for control of the absorption depth of radiation emitted from such an x-ray device as compared to that of a radio-isotope source which always emits in a known and unchangeable (except through decay) manner.

The shape of the anode, and its structure and shielding, determine the directionality of the x-rays emitted. They may be omni directional, or they may be directed radially or axially, or a combination thereof. Anode shaping and tube shielding are well known by those skilled in the art of x-ray generation apparatus. As stated above, the penetration of the x-rays in tissue is directly related to the voltage accelerating the electrons, and the cumulative dose may be controlled by x-ray source beam current and dwell time within the body of the patient. Current variation in the tube controls cathode emission.

Figure 2:
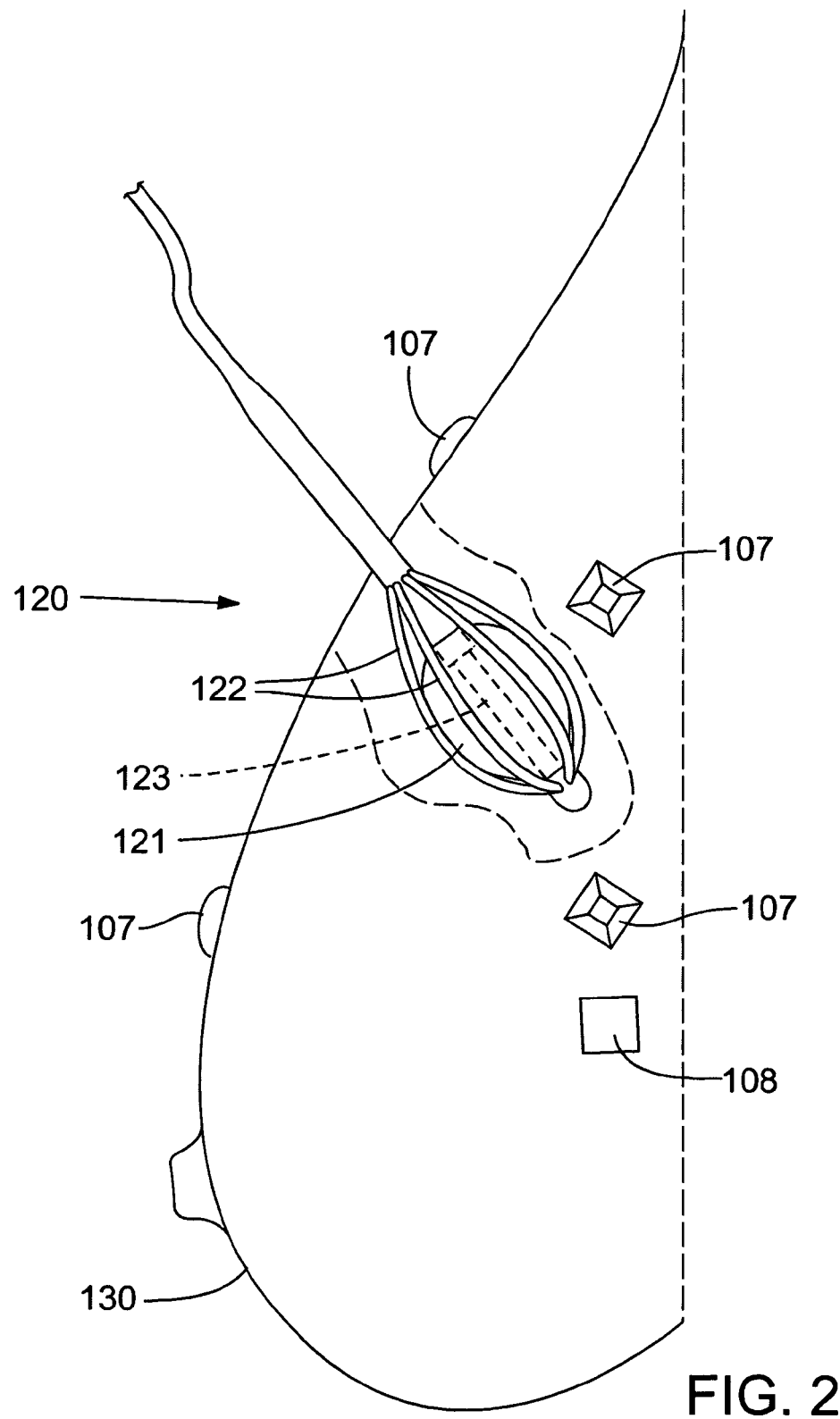
FIG. 2 shows an applicator of the invention in phantom perspective situated within a breast cavity, with on-board guides for radiation sensors and sources as well as surface mounted and interstitial sensors adjacent to the volume of tissue to be treated.

A preferred applicator 120 is shown in FIG. 2, again positioned within a post-operative cavity within the breast 130. The applicator 120 comprises a series of guide tubes 122 on the surface of the balloon 121 and a substantially central guide tube 123, indicated schematically. The summary above describes in some detail the placement of a sensor in the central guide tube 123, and placement of a radiation source 105 or sources in the balloon surface guide tubes 122. For thoroughness, in the discussion which follows, the positioning of the sources and sensors will be reversed from that just mentioned, so that the sensor(s) 106 are in the surface guides 122 (or fixed onto the balloon 121 surface), and the source 105 in the central guide 123. FIG. 2 also shows surface mounted sensors 107 positioned on the breast 130 as well as interstitially placed sensors 108 positioned, for example by needle, within the breast or adjacent to the chest wall.

The source 105 is mounted at the end of a catheter-like structure, comprising a high-voltage cable, as described above, for sequential positioning during creation of the treatment plan and during therapy. Sensors 106 can be mounted on a similar structure or structures, but with electrical conductors or wireless means to power the sensors and/or for communications by the sensors with external system elements, preferably with the processor 101. In one preferred embodiment the sensors are fixed onto the balloon surface, without guides 122. Suitable material for the guide catheter-like structures includes polyurethane. Preferably the sensors are MOSFET type sensors, as by Sicel Technologies, Inc. of Morrisville, N.C. Similar electrical conductors or wireless communications must be provided from surface mounted sensors 107 and interstitial sensors 108 to communicate their readings to the processor. Communications may be continuous, periodic, or in response to interrogation by the processor. If guides are provided, a plurality of sensors may be mounted in a train on the catheter-like structure, or a single sensor may be employed with sequential positioning. Multiple sensor catheters may be employed, such as one per guide, or a single catheter may be used and positioned according to a treatment plan to monitor radiation values, including from different guides and from different positions within single guides.

The controller 104 manipulates the source 105 and sensors 106 according to the treatment plan. This may require that the sensors 106 or sensor trains be positioned sequentially in different guide tubes 122, as well as sequentially positioned along the axis of the guide tubes. The source 105 only need be moved along the axis of the central guide 123. Actuation to achieve manipulation to command from the processor may be accomplished by servomotor, for example.

Figure 3:
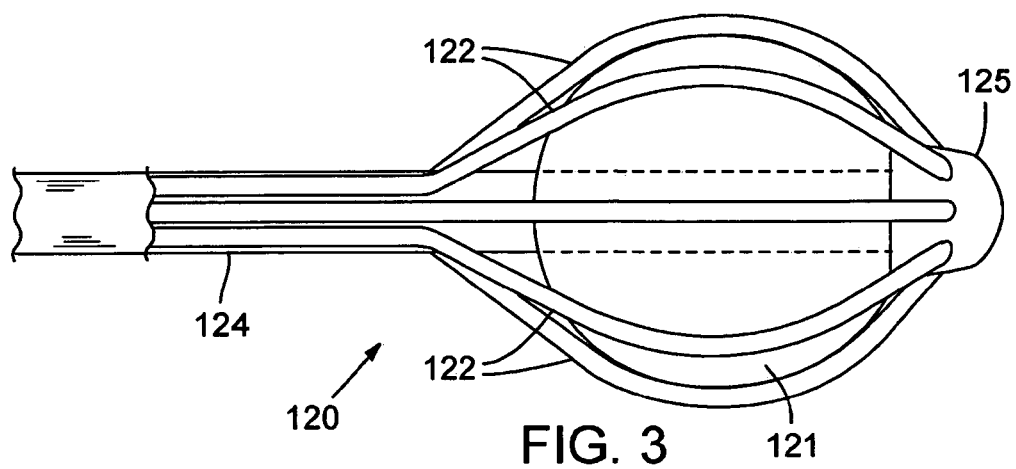
FIG. 3 shows a portion of an applicator in side view.

FIG. 3 shows an applicator 120 in detail with a shaft 124 on which are mounted the balloon 121 distally, terminating in a distal hub 125. The surface guide tubes 122 are positioned on the surface of the balloon 121 and extend proximally where they are secured to or within the shaft 124, for example by bonding, and all of which extend outside the patient. As shown in FIG. 1, all guide tubes 122 and 123 extend to the controller 104 to facilitate source and sensor structure manipulation. Sensor wires, if present, must ultimately communicate with the processor 101, either directly as shown in FIG. 1, or through controller 104 and then to the processor. Similarly, radiation source power connections can be direct to the source catheter structure entering the shaft 124, or they can pass through the controller 104. As shown in FIG. 3, the shaft 124 extends distally into the balloon 121, preferably terminating in the distal hub 125 such that the distal end of the balloon is supported on the shaft, although this is not necessary. The shaft 124 includes a lumen for inflation of the balloon 121, comprising an inflation port outside the patient and an exhaust port within the balloon (neither shown, but typical of those known to one of skill in the art).

Figure 4:
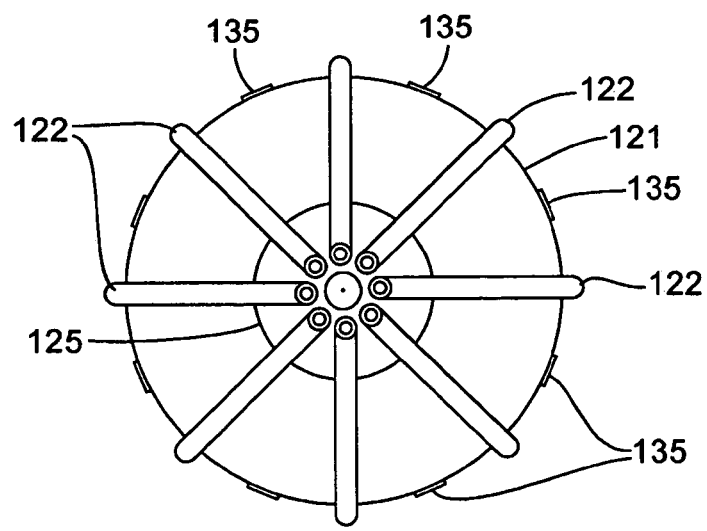
FIG. 4 shows an end view if the applicator of FIG. 3 looking in the proximal direction.

FIG. 4 shows a distal end view looking proximally. The guide tubes 122 are shown spaced around the balloon 121, terminating at the distal hub 125. If desired, one or more of the guide tubes may be reserved as a vent or for suction to remove fluid from within the tissue volume being treated to a vacuum reservoir (not shown) outside the patient. In this instance, the lumina of those tubes would extend through the hub 125 to access any fluid present within the tissue cavity.

FIG. 4 also shows schematically an alternate preferred arrangement wherein dosimeter sensors 135 are shown at exemplary locations fixed onto the balloon. They can be on the inner surface of the balloon if desired.

The method of use of this applicator is similar to that described in the summary above, and may comprise creation of a treatment plan in which a series of incremental locations for each guide within or on the balloon are selected. A source 105 is introduced into the balloon 121 in the axis guide 123 and a sensor 106 or sensors are introduced into sensor guides 122 and advanced onto the surface of the deflated balloon 121, or the sensors are fixed onto the balloon without need for the guides 122. See the summary above for procedure.

As described earlier, the collected data are used in preparation of a treatment plan, wherein the therapist prescribes the local dose, taking account of desired treatment levels for potentially diseased tissue, and radiation resistance of normal tissue which must be protected. The processor 101 then computes the treatment plan to fit the prescription values, taking into account the cumulative radiation incident from each of the specified sensor locations as it will be received from each source location specified in the treatment.

Treatment comprises the controller positioning the source incrementally along the central guide within the inflated balloon. In keeping with the treatment plan, the voltage and current inputs to the source are controlled, as is the dwell in each location.

If demanded by the treatment plan, use of a directional and/or rotating radiation source may be employed to carry out the treatment. Such a source is described in copending application. Shielding may also be used where necessary to protect normal structures adjacent to diseased tissue, and which could be damaged by radiation. Such shielding can be provided for example by coating the balloon selectively by radio opaque elements such as barium, and positioning the shielding adjacent the structure to be protected when positioning the balloon with the treatment cavity.

During treatment, whether fractional or complete, additional sensor readings preferably are taken for verification of treatment to plan and preferably for real-time modifications of plan and treatment. Variances from plan can be signaled to the therapist or to automated portions of the system such that changes may be made to the portions of treatment yet to be administered, they can be made as a treatment session proceeds, or between fractions.

It should be understood that the foregoing relates only to preferred embodiments of the present invention, and that numerous changes and modifications may be made therein without departing from the spirit and scope of the invention as defined in the following claims.

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

I claim:

1. An applicator for delivering ionizing radiation for intracorporeal brachytherapy on a patient, comprising:
   an inflatable balloon, with a shaft connected to and extending into the interior of the balloon,
   the shaft having a conduit for inflating the balloon by admitting fluid to the interior of the balloon,
   a source of ionizing radiation received in and carried within the shaft and inside the balloon for delivery of radiation outwardly through the balloon to the patient's tissue, the source of ionizing radiation comprising a small electronic controllable x-ray source,
   at least one dosimeter sensor at the balloon surface capable of sensing dose received at the sensor from the ionizing radiation source positioned in the shaft at an inward location in the balloon relative to the sensor, and
   communication means for communicating between the sensor and a processor or controller remote from the applicator, for communicating delivered radiation dose information from the sensor to the processor or controller.

2. The applicator of claim 1, wherein the communication means includes a conductor leading from the sensor to a proximal end of the applicator.

3. The applicator of claim 1, wherein the communication means comprises wireless communication.

4. The applicator of claim 1, wherein the balloon has a plurality of such dosimeter sensors located on its surface.

5. The applicator of claim 1, wherein the balloon includes a series of guides on its surface, with a plurality of such dosimeter sensors inserted into the guides.

6. A system for intracorporeal brachytherapy on a patient, comprising:
   an applicator for delivering ionizing radiation, the applicator including
   an inflatable balloon, with a shaft connected to and extending into the interior of the balloon,
   the shaft having a conduit for inflating the balloon by admitting fluid to the interior of the balloon,
   the applicator being capable of receiving a source of ionizing radiation inside the balloon for delivery of radiation outwardly through the balloon to the patient's tissue,
   at least one dosimeter sensor at the balloon surface capable of sensing dose received at the sensor from an ionizing radiation source positioned at an inward location in the balloon relative to the sensor, communication means for communicating between the sensor and a processor or controller remote from the applicator, for communicating delivered radiation dose information from the sensor to the processor or controller, and a processor or controller, and wherein the processor or controller includes a means for modifying the radiation emitted by the source within the balloon in real time as a radiation treatment proceeds, in response to sensed dose information received from the sensor or sensors.

7. The system of claim 6, wherein the modification of radiation emitted from the source includes modification of depth of penetration by modifying voltage applied to the source.

8. The system of claim 7, wherein the modification of radiation emitted from the source includes modification of dose delivered by varying current to the miniature electronic source.

9. An applicator for delivering ionizing radiation for intracorporeal brachytherapy on a patient, comprising:

an inflatable balloon, with a shaft connected to and extending into the interior of the balloon, the shaft having a conduit for inflating the balloon by admitting fluid to the interior of the balloon, a source of ionizing radiation received in and carried within the shaft and inside the balloon for delivery of radiation outwardly through the balloon to the patient's tissue, the source of ionizing radiation comprising a small electronic controllable x-ray source, at least one dosimeter sensor at the applicator capable of sensing dose received at the sensor from the ionizing radiation source positioned in the shaft in the balloon, and communication means for communicating between the sensor and a processor or controller remote from the applicator, for communicating delivered radiation dose information from the sensor to the processor or controller.

10. The applicator of claim 9, wherein the dosimeter sensor is on the shaft of the applicator.

11. The applicator of claim 9, wherein the communication means includes a conductor leading from the sensor to a proximal end of the applicator.

12. The applicator of claim 9, wherein the communication means comprises wireless communication.

* * * * *